United States Patent [19]

Balassubramanyan et al.

[11] 4,315,016

[45] Feb. 9, 1982

[54] HETEROCYCLIC TRIAZOLYLETHYL ETHER COMPOUNDS AND THEIR USE AS PESTICIDES

[75] Inventors: Sugavanam Balassubramanyan, Wokingham; Margaret C. Shephard, Maidenhead, both of England

[73] Assignee: Imperial Chemical Industries Limited, London, England

[21] Appl. No.: 882,205

[22] Filed: Feb. 27, 1978

Related U.S. Application Data

[63] Continuation-in-part of Ser. No. 720,664, Sep. 7, 1976, abandoned.

[30] Foreign Application Priority Data

Sep. 10, 1975 [GB] United Kingdom ............... 37242/75
Sep. 10, 1975 [GB] United Kingdom ............... 37243/75

[51] Int. Cl.$^3$ .................. A01N 43/64; C07D 249/08
[52] U.S. Cl. ...................... 424/269; 548/262; 568/335; 568/655; 568/656; 568/681; 568/686
[58] Field of Search ................... 260/308 R; 424/269; 548/262

[56] References Cited

U.S. PATENT DOCUMENTS

| | | | |
|---|---|---|---|
| 3,394,143 | 7/1968 | Wolf ............................... | 260/308 R |
| 3,647,810 | 3/1972 | Bayer et al. ..................... | 260/299 |
| 3,647,814 | 3/1972 | Greenfield ....................... | 260/308 R |
| 3,658,813 | 4/1972 | Godefroi et al. ................. | 548/341 |
| 3,717,655 | 2/1973 | Godefroi et al. ................. | 548/341 |
| 3,755,349 | 8/1973 | Timmler et al. .................. | 260/308 R |
| 3,812,142 | 5/1974 | Meiser et al. ..................... | 548/341 |
| 3,821,394 | 6/1974 | Timmler et al. .................. | 424/273 |
| 3,897,938 | 7/1975 | Draber et al. .................... | 260/296 |
| 3,912,752 | 10/1975 | Meiser et al. ................... | 260/308 R |
| 3,940,414 | 2/1976 | Kramer et al. ................... | 548/341 |
| 3,952,002 | 4/1976 | Kramer et al. ................... | 260/308 R |
| 4,005,083 | 1/1977 | Buchel et al. .................... | 260/299 |

FOREIGN PATENT DOCUMENTS 2547953  4/1977  Fed. Rep. of Germany ... 260/308 R

*Primary Examiner*—Alton D. Rollins
*Attorney, Agent, or Firm*—Cushman, Darby & Cushman

[57] ABSTRACT

Fungicidal compounds of the formula:

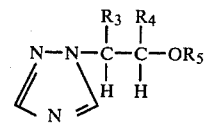

wherein $R_3$ is hydrogen, $R_4$ is phenyl optionally substituted with one halogen, and $R_5$ is alkyl having up to 5 carbon atoms, alkenyl having up to 5 carbon atoms, alkynyl having up to 5 carbon atoms or monochlorophenoxymethyl or $R_5$ is benzyl optionally ring substituted with up to three substituents selected from the class consisting of halogen, alkyl having up to 4 carbon atoms and alkoxy having up to 4 carbon atoms, or a fungicidal acid salt of such a compound.

9 Claims, No Drawings

HETEROCYCLIC TRIAZOLYLETHYL ETHER COMPOUNDS AND THEIR USE AS PESTICIDES

This application is a continuation-in-part of Ser. No. 720,664, filed Sept. 7, 1976, and now abandoned.

This invention relates to heterocyclic compounds which are 1,2,4-triazole compounds, to plant fungicidal compositions containing them and to methods of combating plant fungal pests using them.

The compounds have the general formula (I):

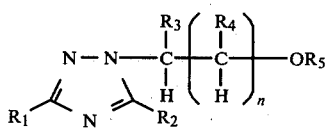

wherein each of $R_1$ and $R_2$, which may be the same or different, is hydrogen, halogen, nitro or alkyl (e.g. methyl, ethyl, propyl or butyl); $R_3$ is hydrogen, alkoxycarbonyl (e.g. methoxy or ethoxy-carbonyl) or substituted or unsubstituted hydrocarbyl or hydrocarboxyloxy, $R_4$ is phenyl or halophenyl, $R_5$ is hydrogen, alkanoyl (e.g. acetyl or propionyl) or substituted or unsubstituted hydrocarbyl, n is 0 or 1, $R_5$ being substituted or unsubstituted hydrocarbyl when n is 0 and $R_3$ being other than substituted or unsubstituted hydrocarbyl when n is 1; or salts of such compounds.

The compounds can contain chiral centre(s). Normally the compounds are prepared in the form of racemic mixtures. However these and other mixtures can be separated into the individual isomers by methods known in the art.

The halogen can be fluorine, chlorine, bromine or iodine.

The hydrocarbyl and hydrocarbyloxy groups may be saturated or unsaturated, straight or branched chain or cyclic or acyclic. Examples are alkyl, alkenyl, alkynyl, cycloalkyl, aryl, aralkyl, aralkenyl or alkaryl, and their hydrocarbyloxy equivalents.

When a hydrocarbyl or hydrocarbyloxy group is, or contains, an aryl (e.g. it is a benzyl or phenyl) group, the latter can be substituted by halogen, alkyl, nitro, trifluoromethyl, cyano, alkoxy or alkylenedioxy (e.g. methylenedioxy).

When $R_3$ and $R_5$ are hydrocarbyl, they are preferably $C_{1-8}$, e.g. $C_{1-7}$, hydrocarbyl; examples are methyl, ethyl, propyl (n- or i-propyl), butyl (n-, i- or t-butyl), amyl (e.g. isopentyl), hexyl (e.g. 3,3-dimethylbutyl), heptyl, allyl, propynyl (e.g. propargyl), phenyl, tolyl (e.g. p-tolyl), nitrophenyl (e.g. o-nitrophenyl), chlorophenyl (e.g. p-chlorophenyl) benzyl or α-methylbenzyl. $R_4$ is preferably chlorophenyl, e.g. p-chlorophenyl or 2,4-dichloro-phenyl.

A preferred class of compounds are those of general formula:

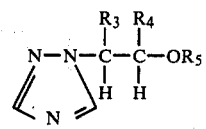

wherein $R_3$ is hydrogen, $R_4$ is phenyl optionally substituted with one halogen, and $R_5$ is alkyl having up to 5 carbon atoms, alkenyl having up to 5 carbon atoms, alkynyl having up to 5 carbon atoms or monochlorophenoxymethyl or $R_5$ is benzyl optionally ring substituted with up to three substituents selected from the class consisting of halogen, alkyl having up to 4 carbon atoms and alkoxy having up to 4 carbon atoms, or fungicidal acid salts of such compounds. Suitably $R_4$ is phenyl, monochlorophenyl (e.g. p-chlorophenyl) or monofluorophenyl (e.g. p-fluorophenyl), and $R_5$ is butyl (e.g. n-butyl), propenyl (e.g. allyl), propynyl (e.g. propargyl), benzyl, monofluorobenzyl (e.g. p-fluorobenzyl), monochlorobenzyl (e.g. m- or p-chlorobenzyl), dichlorobenzyl (e.g. 2,4-dichlorobenzyl), monobromobenzyl (e.g. p-bromobenzyl), monofluoro- monochlorobenzyl (e.g. 2-chloro-4-fluorobenzyl), monomethoxybenzyl (e.g. o-methoxybenzyl) or chlorophenoxymethyl (e.g. p-chlorophenoxymethyl).

Another preferred class of compounds are those of general formula:

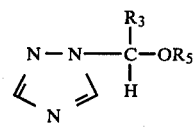

wherein $R_3$ is hydrogen, alkyl having up to 5 carbon atoms, phenyl optionally substituted with one substituent selected from the class consisting of halogen, nitro or alkyl having up to 4 carbon atoms, or benzyl optionally substituted on the α-carbon atom with alkyl having up to 4 carbon atoms, and $R_5$ is alkyl having up to 5 carbon atoms, alkenyl having up to 5 carbon atoms or phenyl optionally substituted with one halogen, or fungicidal acid salts or such compounds. Suitably $R_3$ is hydrogen, methyl, ethyl, propyl (e.g. i-propyl), butyl (e.g. n-butyl), phenyl, monochlorophenyl (e.g. p-chlorophenyl), mononitrophenyl (e.g. o-nitrophenyl), tolyl (e.g. p-tolyl), benzyl or α-methylbenzyl, and $R_5$ is methyl, ethyl, propyl, butyl (e.g. n-butyl), propenyl (e.g. allyl) or monochlorophenyl (e.g. p-chlorophenyl).

The salts of the compounds can be salts of organic or inorganic acids e.g. hydrochloric, nitric, sulphuric, p-toluenesulphonic, acetic or oxalic acid.

Examples of suitable triazole compounds are shown in Table I.

TABLE I

| COMPOUND NO | $R_1$ AND $R_2$ | $R_3$ | n | $R_4$ | $R_5$ | MELTING (OR BOILING*) POINT (°C.) |
|---|---|---|---|---|---|---|
| 1 | H | H | 0 | — | p-Cl—$C_6H_4$ | 59–61° |
| 2 | H | Me | 0 | — | $CH_2$—CH=$CH_2$ | |
| 3 | H | n-Bu | 0 | — | $CH_2$—CH=$CH_2$ | (110°/0.5 mm) |
| 4 | H | Me | 0 | — | n-Bu | (70–75°/0.1 mm) |
| 5 | H | i-Pr | 0 | — | Et | (60°/0.5 mm) |
| 6 | H | $C_6H_5$ | 0 | — | Et | (90°/0.5 mm) |
| 7 | H | p-Cl—$C_6H_4$ | 0 | — | Et | (135–140°/0.1 mm) |

TABLE I-continued

| COMPOUND NO | R₁ AND R₂ | R₃ | n | R₄ | R₅ | MELTING (OR BOILING*) POINT (°C.) |
|---|---|---|---|---|---|---|
| 8 | H | o-NO₂—C₆H₄ | 0 | — | Et | (170–175°/0.3 mm) |
| 9 | H | p-Me—C₆H₄ | 0 | — | Et | (150–160°/0.5 mm) |
| 10 | H | n-Bu | 0 | — | n-Bu | (90–92°/0.2 mm) |
| 11 | H | C₆H₅ | 0 | — | n-Bu | (150°/0.4 mm) |
| 12 | H | p-Cl—C₆H₄ | 0 | — | n-Bu | (150°/0.1 mm) |
| 13 | H | —CH(CH₃)C₆H₅ | 0 | — | Et | (140°/0.1 mm) |
| 14 | H | —CH(CH₃)C₆H₅ | 0 | — | n-Bu | (150°/0.1 mm) |
| 15 | H | C₆H₅CH₂ | 0 | — | Me | (110–120°/0.2 mm) |
| 16 | H | i-Pr | 0 | — | n-Bu | (60°/0.1 mm) |
| 17 | H | Me | 0 | — | p-Cl—C₆H₄ | (100–110°/0.5 mm) |
| 18 |  |  |  |  |  |  |
| 19+ | H | H | 1 | p-Cl—C₆H₄ | —CH₂CH=CH₂ | 113–115° |
| 20 | H | H | 1 | p-Cl—C₆H₄ | n-Bu | (135–140°/0.5 mm) |
| 21 | H | H | 1 | p-Cl—C₆H₄ | CH₂C₆H₅ | 82–84° |
| 22 | H | H | 1 | p-Cl—C₆H₄ | CH₂C≡CH | 105–108° |
| 23 | H | H | 1 | p-Cl—C₆H₄ | CH₂CH=CH₂ | (160°/0.1 mm) |
| 24 | H | H | 1 | p-Cl—C₆H₄ | p-Cl—C₆H₄CH₂ | 112–113° |
| 25 | H | H | 1 | p-Cl—C₆H₄ | 2,4-diCl—C₆H₃CH₂ | 86–87° |
| 26 | H | H | 1 | p-Cl—C₆H₄ | p-F—C₆H₄CH₂ | 66–68° |
| 27 | H | H | 1 | p-Cl—C₆H₄ | p-Br—C₆H₄CH₂ | 116–117° |
| 28 | H | H | 1 | p-Cl—C₆H₄ | 2-Cl—4-F—C₆H₃CH₂ | 103–105° |
| 29 | H | H | 1 | C₆H₅ | C₆H₅CH₂ | 52–54° |
| 30 | H | H | 1 | C₆H₅ | p-Cl—C₆H₄CH₂ | 58–50° |
| 31 | H | H | 1 | C₆H₅ | p-F—C₆H₃CH₂ | 41–43° |
| 32 | H | H | 1 | C₆H₅ | p-Br—C₆H₄CH₂ | 54–56° |
| 33 | H | H | 1 | C₆H₅ | 2,4-diCl—C₆H₃CH₂ | 110–114° |
| 34 | H | H | 1 | p-F—C₆H₄ | CH₂CH=CH₂ | oil |
| 35 | H | H | 1 | p-F—C₆H₄ | n-Bu | oil |
| 36 | H | H | 1 | p-F—C₆H₄ | C₆H₅CH₂ | 74–75° |
| 37 | H | H | 1 | p-F—C₆H₄ | p-Cl—C₆H₄CH₂ | 110–112° |
| 38 | H | H | 1 | p-F—C₆H₄ | p-F—C₆H₄CH₂ | 75–77° |
| 39 | H | H | 1 | p-F—C₆H₄ | 2,4-diCl—C₆H₃CH₂ | 78–81° |
| 40 | H | H | 1 | C₆H₅ | 2-Cl—4-F—C₆H₃CH₂ | 63–65° |
| 41 | H | H | 1 | C₆H₅ | m-Cl—C₆H₄CH₂ | oil |
| 42 | H | H | 1 | C₆H₅ | o-MeO—C₆H₄CH₂ | oil |
| 43 | H | H | 1 | C₆H₅ | p-Cl—C₆H₄OCH₂ | oil |
| 44 | H | H | 1 | C₆H₅ | CH₂CH=CH₂ | oil |

*Boiling points determined by Short Path Distillation

The triazole compounds wherein n is O may be made by reacting 1,2,4-triazole, appropriately substituted if necessary, with the appropriate α-haloether. Thus 1,2,4-triazole may be reacted with a compound of general formula (II):

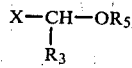

wherein X is halogen, preferably bromine or chlorine, and R₃ and R₅ are as defined above.

This process may in some cases be carried out by heating the reactants together in the absence of a solvent or diluent, but preferably a solvent is present. Suitable solvents are non-hydroxylic solvents [e.g. acetonitrile (which is preferred), dimethylformamide, dimethyl sulphoxide, sulpholane and tetrahydrofuran]. Hydroxylated solvents (e.g. methanol and ethanol) may be used in certain circumstances when the presence of the hydroxyl group does not interfere with the progress of the reaction. The process may also be carried out in the presence of a base, but preferably excess triazole is present to remove liberated HX from the reaction.

The process may also be carried out by reacting the α-haloether, especially if it is an unstable one, in situ with the 1,2,4-triazole dissolved in a non-hydroxylic solvent, preferably acetonitrile.

The α-haloether starting materials may be prepared by methods known in the art.

The triazole compounds wherein n is 1 and R₃ is other than alkoxycarbonyl may be made by reacting an appropriately substituted α-haloketone with triazole, appropriately substituted if necessary, in a hydroxylic or non-hydroxylic solvent and in the presence of a base such as an alkali metal alkoxide, metal hydride (preferably sodium hydride) or tertiary amine. The resulting triazolyl ketone may be reduced to the alcohol [i.e. a compound of general formula (I) wherein R₅ is hydrogen] with e.g. sodium borohydride. The alcohol derivatives (i.e. the compounds wherein R₅ is alkanoyl or substituted or unsubstituted hydrocarbyl) may be made from the alcohol in known manner. The reactions involved are illustrated below:

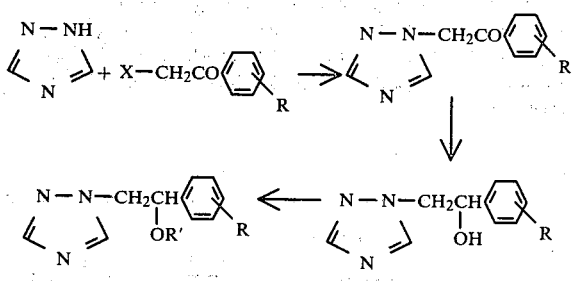

wherein R is hydrogen or halogen, X is halogen and R¹ is optionally substituted hydrocarbyl.

The compounds wherein n is 1 and R₃ is alkoxycarbonyl may be prepared by reacting at low temperature in the presence of a base (preferably lithium diisopropylamide) a compound of general formula (III):

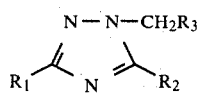

wherein $R_1$ and $R_2$ are as defined above and $R_3$ is alkoxycarbonyl (e.g. ethoxycarbonyl), with an unsubstituted or halo-substituted benzaldehyde, to give an alcohol of general formula (I) wherein $R_3$ is alkoxycarbonyl and $R_5$ is hydrogen, which can then if desired be converted in known manner to the alcohol derivatives wherein $R_5$ is alkanoyl or substituted or unsubstituted hydrocarbyl.

The starting materials for these processes may be made in known manner.

The compounds are active fungicides, particularly against the following diseases:

*Piricularia oryzae* on rice

*Puccinia recondita* and other rusts on wheat and rusts on other hosts

*Plasmopara viticola* on vines

*Erysiphe graminis* (powdery mildew) on barley and wheat and other powdery mildews on various hosts such as *Sphaerotheca fuliginea* on cucumbers, *Podosphaera leucotricha* on apples and *Uncinula necator* on vines

*Botrytis cinerea* (grey mould) on tomatoes, strawberries, vines and other hosts Some of the compounds (e.g. Compounds 19 and 21) have also shown a broad ring of activities against fungi in vitro. Further some of the compounds are active in the form of seed dressings against:

Fusarium spp., Septoria spp., Tilletia spp., and Pyrenophora spp. on cereals.

The compounds also have certain anti-bacterial and anti-viral activities as well as herbicidal activity.

They may be used as such for anti-fungal purposes but are more conveniently formulated into compositions for such usage.

The invention therefore also provides a fungicidal composition comprising, as an active ingredient, a triazole compound or salt thereof, and a carrier for the active ingredient.

The invention also provides a method for combating pests, which are fungal diseases in a plant, which method comprises treating the plant, seed of the plant or the locus surrounding the seed or plant, with a triazole compound or salt thereof as hereinbefore defined.

The compounds can be used to combat plant pests and treat plants or seeds in a number of ways, for example they can be applied, formulated or unformulated, directly to the foliage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foilage, stems, branches or roots, or to soil surrounding the roots.

The term "treating" as used herein refers to all these modes of application and the term "plant" includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The compounds can be used as mixtures with fertilisers (e.g. nitrogen—or phosphorus—containing fertilisers). Compositions comprising only granules of fertiliser incorporating, for example coated with, the triazole compound, are preferred. The invention therefore also provides a fertiliser composition comprising the triazole compound.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonanionic agents.

Suitable cationic agents are quaternary ammonium compounds for example, (cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates). Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, as well as stabilising agent(s), for example epoxides (e.g. epichlorhydrin).

The following Examples illustrate the invention; the temperatures are given in degrees Centigrade (°C.).

EXAMPLE 1

α-1,2,4,-Triazol-1-yl-p-chloroanisole (Compound 1)

α-Chloro-p-chloroanisole (10.6 g) and 1,2,4-triazole (12.4 g) in acetonitrile (120 ml) were refluxed for 48 hours. After cooling to room temperature, triazole hydrochloride was filtered off and acetonitrile removed at reduced pressure to give a sticky gum which was extracted with hot petroleum ether (80°–100°) and allowed to cool slowly to give colourless prisms of the title compound.

Analysis: Found: C, 51.7%; H, 3.8%; N, 20.3%. $C_9H_8ON_3Cl$. Requires: C, 51.6%; H, 3.8%; N, 20.1%.

EXAMPLE 2

Allyl 1-(1,2,4-triazol-1-yl)-ethyl ether (Compound 2)

Allyl 1-chloroethyl ether (3.6 g; Black and Lander, J.C.S., 1965, 5525) and 1,2,4-triazole (6.9 g) in acetonitrile (75 ml) were refluxed for 6 hours. The solvent was removed under reduced pressure; the residual solid was heated with water and extracted with diethyl ether. The ethereal phase was washed with water and dried over magnesium sulphate, and the solvent was removed. The residual oil was purified by passing through a column of silica gel, eluting with ethyl acetate to give the title compound as a colourless oil.

Analysis: Found: C, 54.13%, H, 7.18%, N, 27.14%. $C_7H_{11}N_3O$. Requires: C, 54.88%; H, 7.24%; N, 27.43%.

EXAMPLE 3

Allyl 1-(1,2,4-triazol-1-yl)-pentyl ether (Compound 3)

Following the procedure of Example 2, allyl 1-chloropentyl ether (3 g) and 1,2,4-triazole (3.8 g) were reacted to give the title compound as a colourless oil, which was purified by distillation.

Analysis: Found: C, 61.50%; H, 8.67%; N, 21.22%. $C_{10}H_{17}N_3O$. Requires: C, 61.51%; H, 8.78%; N, 21.52%.

EXAMPLE 4 n-Butyl 1-(1,2,4-triazol-1-yl)-ethyl ether (Compound 4)

Crude n-butyl 1-chloroethyl ether (Straus and Weber, Ann, 1932, 498, 124) was treated with 1,2,4-triazole (2.4 g) in acetonitrile (50 ml) to give at once a precipitate. The mixture was refluxed for 2 hours. The solvent was removed under reduced pressure. The residue was treated with water and extracted with diethyl ether. The ethereal layer was washed with water and dried over magnesium sulphate, and the solvent was removed to give the title product as a colourless oil, which was shown by GLC to be 95% pure.

EXAMPLE 5

Ethyl 1-(1,2,4-triazol-1-yl)-iso-butyl ether (Compound 5)

The diethylacetal of iso-butyraldehyde (2.8 g) was reacted with acetyl chloride (2.7 g) in the presence of copper bronze; the product was reacted with 1,2,4-triazole (3.0 g) in acetonitrile (50 ml) to give the title compound as a viscous oil which GLC showed to be slightly impure.

Analysis: Found: C, 55.73%; H, 8.81%; N, 23.29%. $C_8H_{15}N_3O$. Requires: C, 56.8%; H, 8.87%; N, 24.8%.

EXAMPLE 6

Ethyl 2-(1,2,4-triazol-1-yl)-benzyl ether (Compound 6)

The diethyl acetal of benzaldehyde (3.6 g) and acetyl chloride (2.5 g) were reacted in the presence of a trace of copper bronze. The product was reacted with 1,2,4-triazole (2.8 g) to give the title compound as a viscous oil which GLC showed to be about 95% pure.

Analysis: Found: C, 62.91%; H, 6.54%; N, 20.13%. $C_{11}H_{13}N_3O$. Requires: C, 65.0%; H, 6.4%; N, 20.7%.

EXAMPLE 7

Ethyl (1,2,4-triazol-1-yl)-p-chlorobenzyl ether (Compound 7)

The diethyl acetal of p-chlorobenzaldehyde (4.28 g) was reacted with acetyl chloride (2.34 g) in the presence of a trace of copper bronze. The product was reacted with 1,2,4-triazole (2.8 g) to give the title compound as a viscous oil.

Analysis: Found: C, 55.47%; H, 4.97%; N, 17.27%. $C_{11}H_{12}ClN_3O$. Requires: C, 55.6%; H, 4.72%; N, 17.7%.

EXAMPLE 8

Ethyl 2-(1,2,4-triazol-1-yl)-m-nitrobenzyl ether (Compound 8)

m-Nitrobenzaldehyde diethyl acetal (3 g) was reacted with acetyl chloride (2 g) in the presence of a trace of copper bronze, and then with triazole (2 g) to give the title compound as a thick oil.

Analysis: Found: C, 52.79%; H, 4.83%; N, 22.01%. $C_{11}H_{12}N_4O$. Requires: C, 53.23%; H, 4.84%; N, 22.58%.

EXAMPLE 9

1-p-chlorophenyl-2-(1,2,4-triazol-1-yl)ethanol (Compound 18)

Step 1: α-Bromo-p-chloroacetophenone (4.64 g) in acetonitrile (50 ml) was treated with 1,2,4-triazole (1.4 g) followed by triethylamine (2 g). The mixture was stirred at room temperature for two hours and refluxed for one hour. The solvent was removed under reduced pressure and the residue was treated with water to give a yellow solid which was filtered, washed with water and dried. Crystallisation from ethanol-petroleum ether (60°–80°) gave α-1,2,4-triazol-1-yl-p-chloroacetophenone as cream coloured plates.

Analysis: Found: C, 54.17%; H, 3.72%; N, 19.09%. $C_{10}H_8ClN_3O$. Requires: C, 54.2%; H, 3.62%; N, 19.00%.

Step 2: A suspension of α-1,2,4-triazol-1-yl-p-chloroacetophenone (4 g) in methanol (12 ml) was treated with sodium borohydride (0.5 g) with cooling and stirring. The mixture was then left at room temperature for 0.5 hour and refluxed for 1 hour. The methanol was removed under reduced pressure and water (25 ml) was added followed by dilute hydrochloric acid (10 ml). The white solid was filtered, washed with water and dried. Crystallisation from ethyl acetate-petroleum ether (60°–80°) gave the title compound as a white crystalline solid.

Analysis: Found: C, 53.51%; H, 4.45%; N, 18.55%. $C_{10}H_{10}ClN_3O$. Requires: C, 53.7%; H, 4.47%; N, 18.8%.

EXAMPLE 10

1-p-Chlorophenyl-1-allyloxy-2-(1,2,4-triazol-1-yl)ethane (Compound 26)

A suspension of sodium hydride (0.5 g; 50%; prewashed with dry diethyl ether) in dry dimethylformamide (10 ml) was treated with 1-p-chlorophenyl-2-(1,2,4-triazol-1-yl)ethanol (2.13 g) in dimethylformamide (10 ml). The mixture was kept at 50° with stirring for two hours to complete the formation of the sodium salt. The mixture was cooled to room temperature and treated with allyl bromide (1.21 g) in dimethylformamide (5 ml). The solution was heated to 50° and kept thereat for 6 hours. The solvent was removed under reduced pressure and water was added to the residue to give a brown oil which was extracted into diethyl ether. The ethereal layer was washed with water and dried over sodium sulphate, and the solvent was removed. The resulting oil was dissolved in diethyl ether and a few drops of concentrated nitric acid were added. After stirring well, a precipitate was filtered off and crystallised from ethanol/diisopropyl ether to give the title compound in the form of the nitrate (Compound 19).

Analysis: Found: C, 47.90%; H, 4.64%; N, 17.25%. $C_{13}H_{14}ClN_3O\cdot HNO_3$. Requires: C, 47.5%; H, 4.47%; N, 16.7%.

Neutralisation of the nitrate salt with sodium bicarbonate gave the free base (Compound 26) as a thick gum.

Analysis: Found: C, 59.57%; H, 5.35%; N, 15.59%. $C_{13}H_{14}N_3O$. Requires: C, 59.20%; H, 5.31%; N, 15.94%.

EXAMPLE 11

1-p-chlorophenyl-1-n-butoxy-2-(1,2,4-triazol-1-yl)ethane (Compound 20)

Following the procedure of Example 9, Step 2, 1-p-chlorophenyl-2-(1,2,4-triazol-1-yl)-ethanol (2.23 g), sodium hydride (440 mg; 50%) and n-butyl bromide (1.37 g) were reacted to give the title compound as an oil.

Analysis: Found: C, 59.64%; H, 6.49%; N, 14.77%. $C_{14}H_{18}ClN_3O$. Requires: C, 60.10%; H, 6.44%; N, 15.00%.

EXAMPLE 12

1-p-Chlorophenyl-1-benzyloxy-2-(1,2,4-triazol-1-yl)-ethane (Compound 21)

Following the procedure of Example 9, Step 2, 1-p-chlorophenyl-2-(1,2,4-triazol-1-yl)-ethanol (4.48 g), benzyl chloride (2.54 g) and sodium hydride (1 g; 50%) were reacted to give the title compound as a crystalline solid.

Analysis: Found: C, 65.27;1 %; H, 5.15%; N, 13.65%. $C_{17}H_{16}ClN_3O$. Requires: C, 65.07%; H, 5.15%; N, 13.40%.

EXAMPLE 13

1-p-Chlorophenyl-1-propargyloxy-2-(1,2,4-triazol-1-yl)-ethanol (Compound 23)

Following the procedure of Example 9, Step 2, 1-p-chlorophenyl-2-(1,2,4-triazol-1-yl)-ethanol (3.35 g), propargly bromide (1.80 g) and sodium hydride (0.8 g; 50%) were reacted to give, after chromatography over silica gel eluting with ethyl acetate and crystallisation from ethyl acetate-petroleum ether (60°–80°), the title compound.

Analysis: Found: C, 60.12%; H, 3.98%; N, 16.25%. $C_{13}H_{10}ClN_3O$. Requires: C, 60.12%; H, 3.85%; N, 16.19%.

EXAMPLE 14

1-p-Chlorophenyl-1-acetoxy-2-(1,2,4-triazol-1-yl)-ethane (Compound 22)

1-p-Chlorophenyl-2-(1,2,4-triazol-1-yl)-ethanol (2.24 g) and triethylamine (1.1 g) in dry diethyl ether (50 ml) were treated with acetyl chloride (0.8 g) in dry diethyl ether (5 ml) and the mixture was stirred for 3 hours at room temperature to give a white solid which was filtered off and washed with ether. The solvent was removed from the filtrate to give a brown oil. The oil was distilled to give the title compound as a semi-solid which could not be purified further.

EXAMPLE 15

Ethyl α-(1,2,4-triazol-1-yl)-α-(p-chlorophenyl)-β-hydroxypropionate (Compound 24)

Diisopropyl amine (3.3 g) in dry diethyl ether (30 ml) was treated under a nitrogen atmosphere at −20° with butyllithium (30 ml of a 7.5% solution in hexane) and the mixture was stirred for 15 minutes. Ethyl α-1,2,4-triazol-1-yl acetate (4.6 g) in dry diethyl ether (30 ml) was added with stirring keeping the temperature below −20°. A white precipitate was formed and the mixture was treated with p-chlorobenzaldehyde (4.2 g) in dry diethyl ether (60 ml) keeping the temperature below −20°. The reaction mixture was stirred at this temperature for 4 hours and left overnight at room temperature. Water was carefully added to the reaction mixture and the ethereal layer was separated. The aqueous layer was neutralised with concentrated hydrochloric acid and extracted with methylene chloride. The combined organic layers were washed with water and dried over sodium sulphate and the solvent was removed. Diethyl ether was added to the residue which was then left in a refrigerator for 24 hours to give a yellow solid. The latter was filtered, washed with ether and dried. Crystallisation from ethanol gave the title compound as a pale yellow solid.

Analysis: Found: C, 52.92%; H, 4.81%; N, 14.14%. $C_{13}H_{14}ClN_3O_3$. Requires: C, 52.78%; H, 4.74%; N, 14.25%.

EXAMPLE 16

Ethyl α-(1,2,4-triazol-1-yl)-β-2,4-dichlorophenyl-β-hydroxypropionate (Compound 25)

Using the procedure of Example 15, ethyl-1,2,4-triazol-1-yl acetate (2.3 g), 2,4-dichlorobenzaldehyde (2.55 g), diisopropylamine (1.65 g) and butyllithium (7.5 ml of 15% solution in hexane) were reacted to give a white solid which was crystallised from ethanol to give the title compound.

Analysis: Found: C, 46.76%; H, 3.95%; N, 13.12%. $C_{13}H_{13}Cl_2N_3O_3$. Requires: C, 47.27%; H, 3.94%; N, 12.73%.

EXAMPLE 17

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 ppm a.i. suspensions were sprayed on to the foliage and applied to the roots of the same plants via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil and foliage one or two days before the plant was inoculated with the diseases. An exception was the test on *Erysiphe graminis,* in which the plants were inoculated 24 hours before treatment. After inoculation, the plants were put into an appropriate environment to allow infection to take place and then incubated until the disease was ready for assessment. The period between inoculation and assessment varied from 3 to 10 days according to the disease and environment.

The disease control was recorded by the following grading:
4=No disease
3=0-5%
2=6-25%
1=26-60%
0=>60%

The resuls are shown in Table II.

TABLE II

| COMPOUND NUMBER | PUCCINIA RECONDITA (WHEAT) | PHYTOPHTHORA INFESTANS (TOMATO) | PLASMOPARA VITICOLA (VINE) | PIRICULARIA ORYZAE (RICE) | BOTRYTIS CINEREA (TOMATO) | ERYSIPHE GRAMINIS (BARLEY) |
|---|---|---|---|---|---|---|
| 1 | 3 | 0 | 0 | 3 | 2 | 3 |
| 2 | 0 | 0 | 0 |   | 0 | 4 |
| 3 | 3 | 1 |   | 3 | 2 | 4 |
| 4 | 0 | 0 | 0 | 3 | 0 | 4 |
| 5 | 0 | 0 | 0 | 0 | 1 | 4 |
| 6 | 0 | 0 | 0 | 3 | 0 | 1 |
| 7 | 0 | 3 | 0 | 2 | 0 | 4 |
| 8 | 0 |   |   | 0 |   | 4 |
| 9 | 0 | 2 | 0 | 2 | 0 | 1 |
| 10 | 3 | 1 | 0 | 3 | 0 | 4 |
| 11 | 0 | 1 | 3 | 0 | 1 | 0 |
| 12 | 4 |   | 0 | 0 | 3 | 4 |
| 13 | 2 | 1 | 2 |   | 0 | 4 |
| 14 | 2 | 0 | 0 | 1 | 1 | 4 |
| 15 | 0 | 0 | 0 | 0 | 2 | 4 |
| 16 | 4 |   | 0 | 2 | 0 | 4 |
| 17 | 4 | 0 | 0 | 1 | 0 | 4 |
| 18 | 0 | 3 |   | 3 | 0 | 4 |
| 19 | 3 | 3 |   | 3 | 3 | 4 |
| 20 | 0 | 1 |   | 0 | 2 | 3 |
| 21 | 3 | 2 | 2 | 0 | 3 | 4 |
| 22 | 3 | 0 | 4 |   | 0 | 4 |
| 23 | 3 | 2 |   | 0 | 0 | 4 |
| 24 | 0 | 0 | 0 | 0 | 1 | 0 |
| 25 | 0 | 0 | 0 | 3 | 3 | 4 |
| 26 | 2 | 1 | 2 | 0 | 3 | 4 |
| 27 | 1 | 1 | 0 | 0 | 0 | 4 |
| 28 | 0 | 1 |   | 0 | 3 | 4 |
| 29 | 2 | 2 |   | 0 | 3 | 4 |
| 30 | 3 | 2 | 0 | 0 | 3 | 4 |
| 31 | 1 | 1 | 2 | 0 | 1 | 0 |
| 32 | 1 | 3 | 0 | 0 | 4 | 4 |
| 33 | 0 | 0 | 0 | 0 | 2 | 4 |
| 34 | 4 | 0 | 0 | 3 | 2 | 4 |
| 35 | 4 | 0 | 0 | 0 | 3 | 4 |
| 36 | 2 | 3 | 0 | 0 | 3 | 4 |
| 37 | 1 | 0 | 0 | 0 | 3 | 4 |
| 38 | 3 | 3 |   | 0 | 4 | 4 |
| 39 | 2 | 1 |   | 0 | 1 | 4 |
| 40 | 1 | 0 | 0 | 2 | 3 | 4 |
| 41 | 2 | 0 |   | 0 | 4 | 4 |

TABLE II-continued

| COMPOUND NUMBER | PUCCINIA RECONDITA (WHEAT) | PHYTOPHTHORA INFESTANS (TOMATO) | PLASMOPARA VITICOLA (VINE) | PIRICULARIA ORYZAE (RICE) | BOTRYTIS CINEREA (TOMATO) | ERYSIPHE GRAMINIS (BARLEY) |
|---|---|---|---|---|---|---|
| 42 | 0 | 0 | 0 | 0 | 1 | 3 |

EXAMPLE 18

Compound 20 was sprayed as a solution in acetone/water onto wheat, barley, tomato, Brussels sprout and soya bean at the rate of 500 p.p.m. to run off. After 10 days, observations were made of the effect of the chemical on the plants. In four instances, a 15 to 20% reduction in growth was noted.

We claim:

1. A compound of general formula:

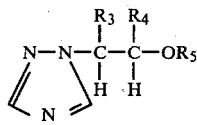

wherein $R_3$ is hydrogen, $R_4$ is phenyl optionally substituted with one or two halogen, and $R_5$ is alkyl having up to 5 carbon atoms, alkenyl having up to 5 carbon atoms, alkynyl having up to 5 carbon atoms or $R_5$ is benzyl optionally ring substituted with halogen, alkyl or alkoxy, or a fungicidal acid salt of such a compound.

2. A compound as claimed in claim 1 wherein $R_4$ is phenyl, monochlorophenyl or dichlorophenyl, and $R_5$ is butyl, propenyl, propynyl, benzyl.

3. A compound as claimed in claim 1 wherein $R_4$ is p-chlorophenyl, and $R_5$ is n-butyl, allyl, propargyl or benzyl.

4. A fungicidal composition consisting essentially of as active ingredient, a fungicidally effective amount of a compound or salt as claimed in claim 1, and a carrier for the active ingredient.

5. A fungicidal composition consisting essentially of, as active ingredient, a fungicidally effective amount of a compound or salt as claimed in claim 2 and a carrier for the active ingredient.

6. A fungicidal composition consisting essentially of, as active ingredient, a fungicidally effective amount of a compound or salt as claimed in claim 3 and a carrier for the active ingredient.

7. A method of combating fungal diseases in a plant, said method consisting essentially of the step of applying to the plant, seed of the plant or to the locus of the plant or seed, a fungicidally effective amount of a compound or salt as claimed in claim 1.

8. A method combating fungal diseases in a plant, said method consisting essentially of the step of applying to the plant, seed of the plant or to the locus of the plant or seed, a fungicidally effective amount of a compound or salt as claimed in claim 2.

9. A method of compating fungal diseases in a plant, said method consisting essentially of the step of applying to the plant, seed of the plant or to the locus of the plant or seed, a fungicidally effective amount of a compound or salt as claimed in claim 3.

* * * * *